United States Patent [19]

Kroner

[11] Patent Number: 4,699,013
[45] Date of Patent: Oct. 13, 1987

[54] SAMPLING DEVICE

[75] Inventor: Karl H. Kroner, Wolfenbüttel, Fed. Rep. of Germany

[73] Assignees: Gessellshaft fur Bio technolgische Forshung mbH, Braunschroeig, Fed. Rep. of Germany; Intermedicat, (GmbH), Emmenbrucke, Switzerland

[21] Appl. No.: 868,352

[22] Filed: May 29, 1986

[30] Foreign Application Priority Data

Jun. 7, 1985 [DE] Fed. Rep. of Germany ....... 3520489

[51] Int. Cl.$^4$ ........................... G01N 1/18; G01N 1/10
[52] U.S. Cl. ................................. 73/863.23; 366/140; 422/101; 210/383; 210/512.3
[58] Field of Search ........... 73/863.23, 863.24, 863.25, 73/863.41, 863.44; 366/140; 436/178; 422/101, 102; 210/512.3, 383, 695, 321.1

[56] References Cited

U.S. PATENT DOCUMENTS 2,020,529 11/1935 Thorsten .......................... 73/863.23
3,801,280 4/1974 Shah et al. ...................... 422/101 X
4,052,163 10/1977 Patzner ............................. 422/101
4,317,726 3/1982 Shapel ............................ 422/101 X
4,417,980 11/1983 Baur et al. ..................... 210/383 X Primary Examiner—Tom Noland

[57] ABSTRACT

The sampling device for chemical, in particular biochemical process technics, consists of a sterilizable container in which a magnetic stirring system is accommodated whose agitator beam may be adjusted in height also in operation. Fluid flows through a tangential inlet near the bottom to be discharged through an outlet provided in the upper end wall. Beneath the filter membrane there is an extremely small dead space through which the filtrate gets to the filtrate outlet. The lower end of the agitator arm is designed as a pointed flow break-away edge which, in case of rotation, generates an alternating pressure field migrating over the membrane. The device is particularly characterized by short response times and by a long service life due to the fact that without a substantial shearing, the filter membrane is kept free from deposits.

19 Claims, 6 Drawing Figures

SAMPLING DEVICE

BACKGROUND OF THE INVENTION a. Field of Invention

The invention relates to a sampling device for the removal of filtered samples from fluids comprising a container including a rotatable agitor above a filter membrane, an inlet ending in the container above the filter membrane and a filtrate outlet for the discharge out of the container beneath the filter membrane.

b. Description of the Prior Art

There have been known agitator cells comprising a magnetic stirring rod pendingly mounted above a filter membrane (AMICON magnetic stirrer cell). The filter membrane rests on a plate having profiles on its surface to evacuate the filtrate. The fluid to be filtered is introduced under pressure through a cover inlet into the container and, by the magnetic stirring rod above the filter membrane, it is kept in movement.

For chemical, in particular biochmeical process technics, there is an ever increasing demand of on-line measuring methods to determine chemical substance parameters in process for monitoring, regulating and controlling purposes and the time between the samping step and the availability of the result should be as short as possible. As a rule, the following four steps are required for performing on-line-analysis:
1. sampling by branching off a representative partial current,
2. preparing the sample (e.g. removing solids or interfering accompanying substances)
3. analytic determination (detection process)
4. evaluation (registration).

The first two partial steps are frequently involved with considerable difficulties if a quick time behavior is required.

As a rule, only a discontinuous sampling of dissolved or gaseous low-molecular components may be effected with the known sampling means. For the representative removal of macromolecules such as proteins and enzymes, the existing systems are unsuited because of occurring phenomena of denaturation and non-controllable coating and clogging problems. Basically, unfavorable long dead times are inherent to dialysis systems because the concentration difference required for the material transport is to be taken into consideration.

In biotechnology, use is made of by-pass systems in a closed cycle, in order to perform for instance a continuous fermentation with cell mass retention for the harvest of cells and for the processing of bio-products. Due to the membrane fouling by adsorption and polarization effects, the use of such techniques or technic is critical for continuous sampling. Further problems result from the normally high dead volumes with respective long response times and by the short service lives.

SUMMARY OF THE INVENTION

It is the object of the invention to provide a sampling device of the aforementioned type which permits a continuous sampling with a substantially uniform permeability of the filter membrane.

The problem is solved according to the invention in that the inlet is provided near the bottom of the container and, is directed tangentially in the container and that the upper end wall of the latter includes an outlet.

By the sampling device of the invention, a constant exchange of the total container volume is possible at a rate which is much higher than the filtration rate. Due to the tangentially arranged inlet, fluid is introduced into the inner container chamber under controlled turbulence, and, above the filter membrane, the agitator produces a continuously changing pressure field to keep off residues from the filter membrane which, by the tangential inlet is constantly exposed to the flow of a high fluid rate. This effect is intensified by the agitator rotating in the sense of the fluid current, thus prohibiting a clogging of the membrane with solids, which, on the contrary, are rinsed away to be removed with the liquid flow through the outlet out of the container. As a result, a uniform filtrate yield and a short response time of the device or system are accompanied by its long service life.

Preferably, the outlet is provided at the side opposite to the inlet and at a point higher than the inlet so that freshly fed fluid first sweeps over the filter membrane to subsequently rise and finally get, after a repeated rotation above the filter membrane, to the outlet. The sampling device allows an optimum control of the cover layer formation on the filter membrane. By the cooperation of the stirring beam rotating closely above the filter membrane, in conjunction with the tangential inlet, an oriented turbulence field is formed at the filter membrane. The distance between the stirring beam and the filter membrane is such as to avoid shearing at the filter membrane thus decoupling from one another the overflowing of the membrane and the flowing through the device. The amount of filtrate does not depend on in the static service pressure but on the dynamic alternating pressure generated by the agitator. It is possible accordingly to optionally select within certain limits the static service pressure which may be kept very low.

To obtain a low clearance volume and a corresponding short response time of the system, the bottom of the container comprises a groove extending from the bottom center to the filtrate outlet, and directly on the bottom, there is provided a plate as a membrane support having a plurality of holes, its underside including channels corresponding to said holes. Thus, the clearance volume is substantially dictated by the volume of the channels. After having passed the membrane, the filtrate may quickly flow to the filtrate outlet and, as a result, from all sides of the bottom, liquid may be evacuated along the shortest possible way to the filtrate outlet. Suitably, the channels extend radially, and their inner ends are connected to a collecting chamber formed in the central region at the underside of the plate.

The diameters of the holes are reduced towards the plate periphery to permit a uniform filtrate removal representatively over the cross section of the plate.

The upper side of the plate conveniently contains an inclined edge to press thereagainst a sealing ring. The plate is flat to the outside. The sealing ring does not only serve for sealing the system externally but also for fixing the filter membrane on the marginal area of the plate.

According to a preferred embodiment of the invention, the cross section of the stirring rod is tapered downwardly and its lower end contains a flow breakaway edge which moves at a controlled distance at a high speed (300 to 500 rpm) above the filter membrane to thus generate an alternating pressure field to expel fluid through the filter membrane. The flow break-way edge extending vertically has a cross section which preferably forms an angle of about 60°.

The outlet is situated at the highest point of the inside of the upper end wall of the container. The central region of said end wall contains a projection protruding towards the container inside, thus preventing air bubbles being formed in the process current of bioreactors from interfering with the mixing effect, said air bubbles traveling up in the container to be discharged through the outlet.

The used agitator is preferably a magnetic stirrer whih contains a stirring beam adjustable in height during the rotation.

BRIEF DESCRIPTION OF THE DRAWINGS

One embodiment of the invention will be explained in more detail with reference to the enclosed drawings in which.

DESCRIPTION OF THE PREFERRED EMBODIMENT

Figure 1:
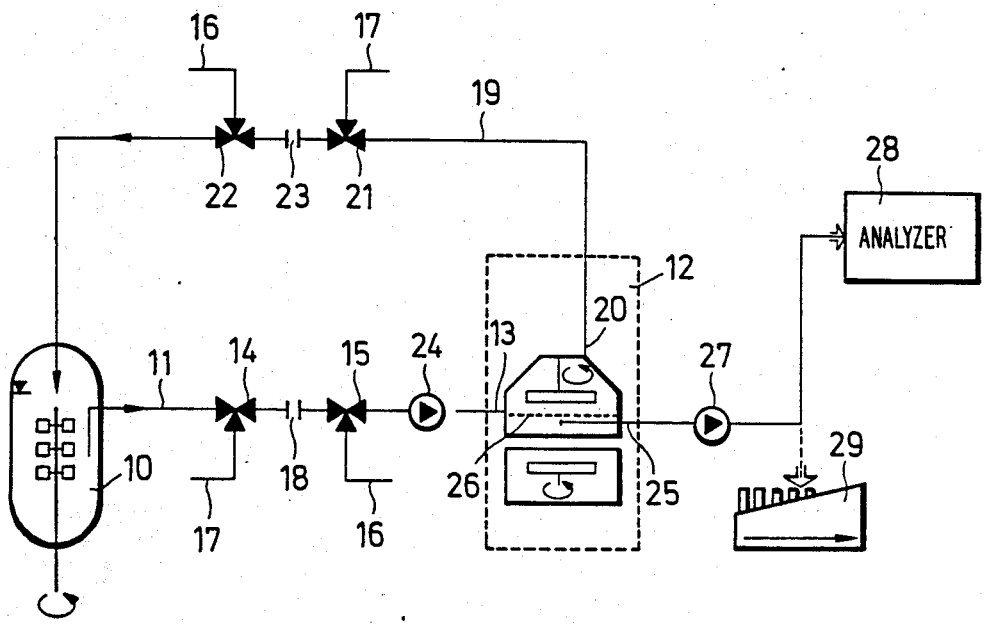
FIG. 1 is a schematic view of a device for continuous sampling.
Figure 2:
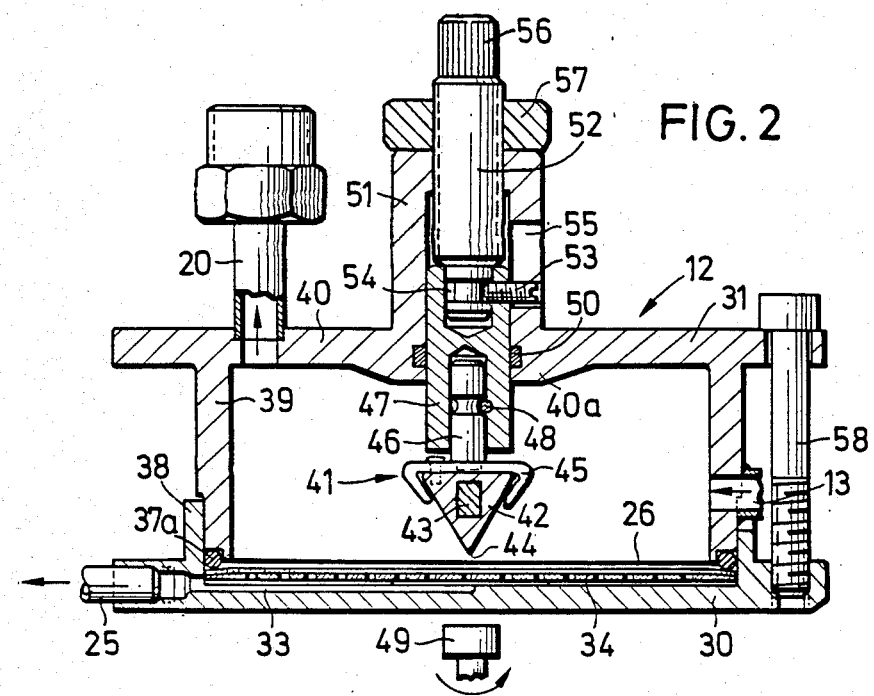
FIG. 2 is a vertical section of the sampling device.
Figure 3:
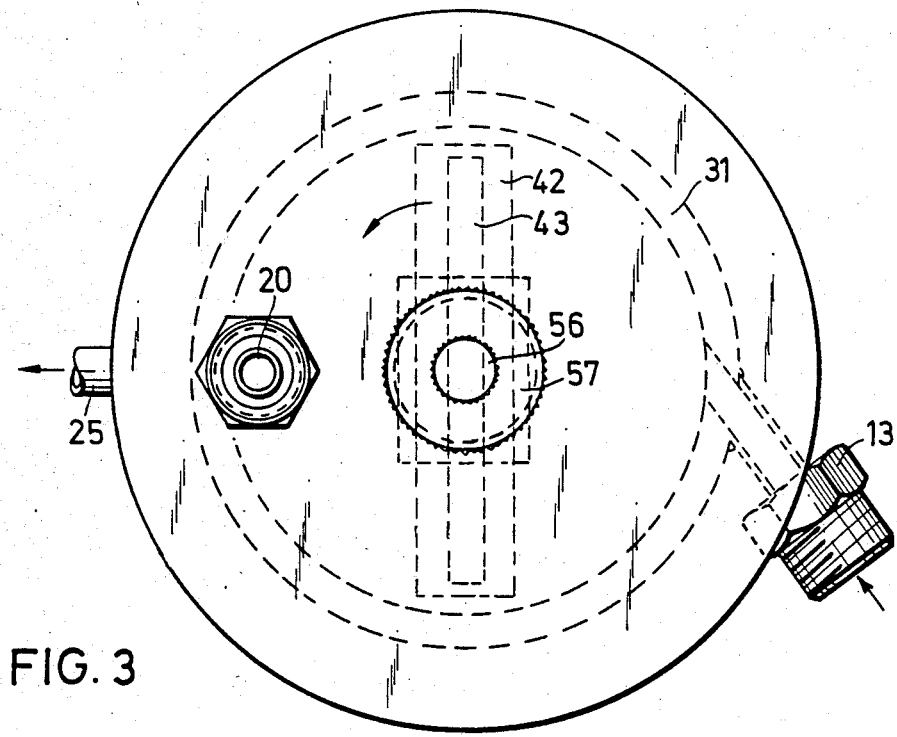
FIG. 3 is a plan view of the sampling device.

As evident from FIG. 1, there is provided a bioreactor 10 whose outlet is connected via line 11 to the inlet 13 of the sampling device 12, said line 11 containing two directional control valves 14 and 15 of which valve 14 is connected to a vapor line 17, while valve 15 is connected to the vapor discharge line 16. A check valve 18 is arranged between valves 14 and 15.

Similarly, two directional control valves 21 and 22 having a check valve 23 intermediate them are provided in line 19 which connects outlet 20 of the sampling device 12 to the inlet of the bioreactor 10. Sterilizing vapor may be delivered through valve 22 to the bioreactor 10, while the outlet 20 of the sampling device may be connected via the directional control valve 21 to the vapor outlet line 17. Between the directional control valve 15 and inlet 13, there is provided a pump 24.

For the sterilization of bioreactor 10 or of the sampling device 12, check valves 18 and 23 are closed thus allowing a sterilizing vapor through the bioreactor 10 and/or through the sampling device 12. At the same time, lines 11 and 19 as well as pump 24 are also sterilized.

For a continuous sampling from the bioreactor 10, fluid is pumped by pump 24 from the bioreactor to the sampling device 12, said fluid leaving the sampling device through outlet 20 to be recycled to the bioreactor 10. In the sampling device 12, solids are retained in the closed cycle between bioreactor and sampling device, while the filtrate having passed filter membrane 26, is fed via filtrate outlet 25 and pump 27 to the analyser 28 and to a fraction collector 29.

Figure 4:
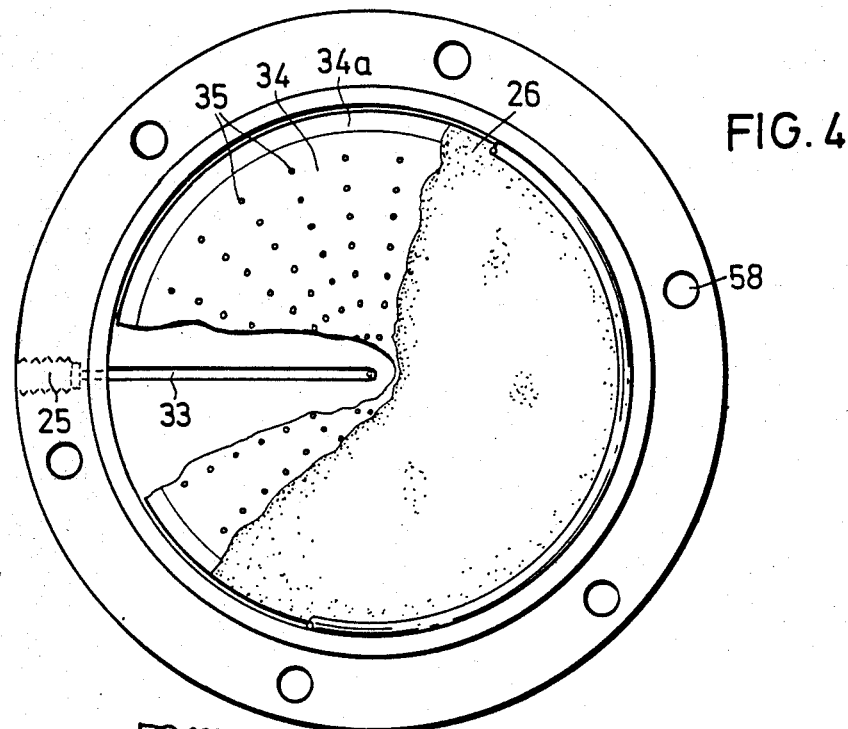
FIG. 4 is a plan view of the bottom part of the sampling device with removed upper portion.
Figure 5:
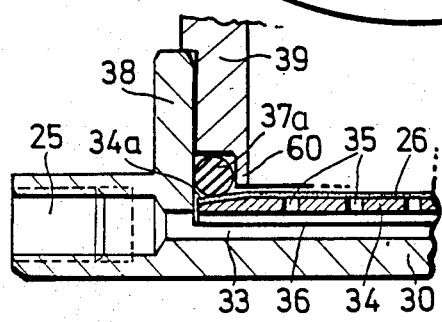
FIG. 5 is an enlarged cross section of the filtrate outlet region and FIG. 6 is a view of the underside of the plate serving as a membrane support.
Figure 6:
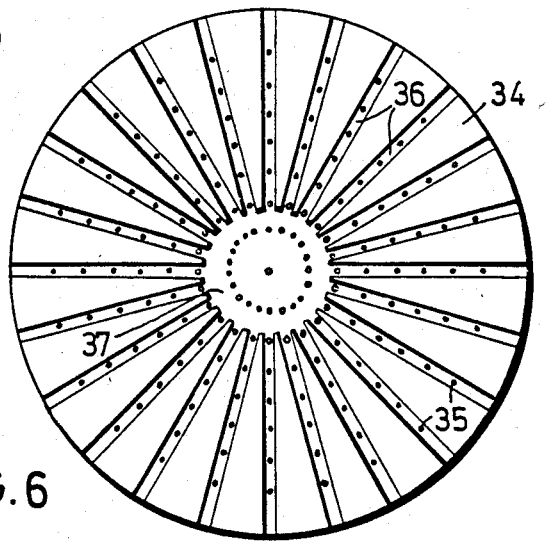

Sampling device 12 shown in FIGS. 2 to 6 comprises a container consisting of a lower part 30 and an upper part 31, the lower part being formed of a cylindrical tub having a flat bottom including a radial groove 33 extending from the center to the filtrate outlet 25. On the bottom of the lower part 30, there rests flatly plate 34 serving as a support for filter membrane 26 and having a plurality of holes 35 which extend along radial lines. On the bottom surface of plate 34 there are a plurality of radial channels 36 corresponding to holes 35 as shown in FIG. 6. Each channel has an outer end which is open at the edge of the plate. The inner ends of the channels form a collecting chamber 37 disposed at the center of the plate 34. The collecting chamber 37 is as deep as channels 36. Some of the holes 35 are ending in the central region of the plate, the diameters of the holes 35 being reduced closer to the container axis than the diameters of the holes farther from the container axis.

As evident from FIGS. 4 and 5, the border 34a of the plate is flattened to the outside. A sealing ring 37a presses the border of the filter membrane 26 against the border 34a of the plate 34, said sealing ring 37a additionally sealing the gap between the peripheral wall 38 of the lower part 30 and the peripheral wall 39 of the upper part 31. The cylindrical peripheral wall 39 is inserted into the peripheral wall 38. Its lower end comprises a recess limited inwardly by an axial stem 60 to receive the sealing ring 37a. Said stem 60 adapted to elongate the inside of the peripheral wall 39 and it terminates closely above the filter membrane 26.

The peripheral wall 39 of the upper part 31 includes the inlet 13 ending tangentially in the container inside, the term "tangentially" meaning that the direction of the channel formed by the inlet 13 does not point to the longitudinal axis of the container and that the inflowing fluid is introduced into the container inside at least approximately parallel to the peripheral wall 39 so as to circulate along the peripheral wall. Inlet 13 is situated in the lower half of the container.

Outlet 20 provided at the upper end wall 40 of the top part 31 is positioned at the highest point of the inner container space. The central region of the end wall 40 comprises a projection 40a extending into the container. Air bubbles introduced into the container travel up into the annular space around the projection 40a to be evacuated through the outlet 20.

The agitator 41 dipping coaxially into the container consists of a horizontal agitator beam 42 containing a magnet 43, the cross section of the agitator beam 42 which extends nearly over the total diameter of the inner container space being triangular with a tip pointing downward and forming the flow break-away edge 44 that is arranged above the filter membrane 26. The edge 44 is of an acute-angle design at which the flow of liquid breaks away if the agitator beam 42 is rotating. The angle at the flow break-away edge 44 is 60°.

The agitator beam 42 consisting of polytetrafluoroethylene and is secured by means of a clamp 45 to a vertical piece 46 positioned to be freely rotatable in sleeve 47. Part of the periphery of a tangential pin 48 secured in sleeve 47 extends into an annular groove of piece 46 to protect said piece against axial displacements. The agitator beam 42 is moved by a driving magnet 49 situated in a drive unit beneath the container and acting with its magnetic field on the magnet 43 contained in the agitator beam 42. Sleeve 47 extends into the tubular attachment 51 of the housing through a bore of end wall 40 sealed by seal 50. Pin 52 is adjustable by means of its external thread in an internal thread of the attachment 51 and it extends into the upper end of sleeve 47. A bolt 53 screwed into the wall of sleeve 47 extends into a groove 54 of the adjusting pin 52 to secure said sleeve against axial displacements of the adjusting pin 52 by permitting rotations of the pin relative to the sleeve. The external end of bolt 53 is guided in a vertical slot 55 of the attachment 51. The position of bolt 53 allows to note the height of the agitator arm 42 above the membrane 26.

The external end of the adjusting pin 52 is provided with a knob 56. Further, a counternut 57 is externally screwed on the outer thread of the adjusting pin 52.

By rotating knob 56, the height of the agitator arm 52 above the membrane 26 may be changed even during the operation of the magnetic stirring device 41. This is of importance in case of on-line-operation because it is necessary occasionally to change the height of the agitator arm without interrupting the continuous flow. Further, in service, the separating operation may be adapted to compensate for probable changes of the process fluid (e.g. solid content, viscosity).

The upper housing part 31 and the lower housing part 30 are interconnected by screws 58 passing through respective external flanges of both housing parts.

A flat holddown means (not shown) may be placed above the filter membrane to inhibit vault formations of the filter membrane.

In operation of the sampling device, fluid from the bioreactor 10 is fed into the inlet 13 to flow through the inner container and leave through the upper outlet 20. By the symmetrically downwardly directed flow breakaway edge 44 of the rotating agitator beam 42, an alternating pressure field is generated above the filter membrane 26 and is superimposed on the static pressure inside the container. Due to the alternating pressure field, there is formed a pressure peak migrating in cycles above membrane 26 and pressing the filtrate through the membrane. A suction force formed behind the pressure peak becomes effective in whirling up solids which have settled on the membrane to return them into the cycling fluid current. By this means, no deposits may remain on the membrane.

The dead volume beneath the membrane 26 is formed by volumes of holes 35 and channels 36 as well as by the collecting space 37 and groove 33, said dead volume being very low, e.g. 2 ml.

This is necessary because of the relatively low transmembrane flow rate (between 0.3 to $4 \times 10^{-4}$ cm/s). It is possible to reach dead times of 2 min and response times of $\leq 10$ min in case of sudden changes of concentrations. Thus, concentration gradients of $\geq =5\%$/min may be still reproduced free of distortions.

The container as well as all elements accommodated therein consist of vapor-sterilizable material, e.g. steel or Teflon.

The substantial data of a sampling device realised in practice are listed hereunder:
 volume: about 200 ml
 membrane surface: about 63 cm$^2$
 diameter: about 90 mm
 speed: 300 to 600 rpm
 service pressures: 0.1–0.4 bar
 feed rate: 20–30 l/h
 filtrate rate: 0.1–1 ml/min
 dead time: about 2 min
 signal gradient: $\geq 5\%$ min$^{-1}$ The most important advantages of the sampling device of the invention as compared to prior art are indicated hereunder once more:
in-situ-evaporable, autoclavable, sterilizable
simple coupling, accessible at any time
low maintenance cost (setting period 30 min)
effective control of membrane coating by agitator adjustable in height
magnetic drive (no shaft passage)
low control cost
high service life (even with complex fluids)
aseptic operation
free membrane choice
decoupling of overflow of membrane and throughflow of module (irrespective of process flow)
low rates of flow (reduced pumping capacity)
low influence on process flow
solid-free filtrate (continuously)
low delay times (no distortion of concentration profiles by back mixing)
coupling of various analyzers,
stainless steel design
operation possible by simple lab means (pumps, magnetic stirrer)
representative removal also of macromolecules.

We claim:

1. A sampling device for removal of filtered samples from fluids, comprising:
 a container having a bottom, a vertical wall coupled to said bottom, an upper end wall coupled to said vertical wall, an inlet disposed in said vertical wall, a filtrate outlet, a groove extending from a center of said bottom to said filtrate outlet, and a second outlet disposed in said upper wall;
 a filter membrane disposed at said bottom of said container,
 said inlet being disposed above said filter membrane proximate said bottom of said container, and substantially tangential to said vertical wall, said filtrate outlet being disposed beneath said filter membrane; and,
 a rotatable agitator, disposed above said filter membrane, and coupled to said upper end wall.

2. A sampling device as in claim 1 wherein said second outlet is disposed at a side of said container opposite said inlet.

3. A samping device as in claim 2 further comprising a plate disposed between said bottom of said container and said filter membrane, supporting said filter membrane, having a plurality of radial channels disposed on a bottom thereof, and having a plurality of holes disposed therethrough opening into said channels.

4. A sampling device as in claim 3 wherein said plate comprises a collection chamber disposed centrally in said bottom of said plate, said channels terminating in said collection chamber.

5. A sampling device as in claim 4 wherein said holes decrease in size towards a periphery of said plate.

6. A sampling device as in claim 5 wherein an upper surface of said plate includes a downwardly inclined border, and further comprising a sealing ring disposed above and in contact with said border.

7. A sampling device as in claim 6 wherein said rotatable agitator comprises a horizontally disposed beam having a cross section tapered downwardly, and a lower end with a flow break-away edge.

8. A sampling device as in claim 7 wherein said flow break-away edge is disposed vertically, and a cross section of said edge forms an angle of substantially 60°.

9. A sampling device as in claim 8 wherein said second outlet is disposed at a highest point on an inside surface of said upper end wall, and wherein said upper end wall includes a projection disposed centrally therein and protruding into an inside of said container.

10. A sampling device as in claim 9 wherein said rotatable agitator further comprises a magnet disposed in said beam so that said agitator is drivable by a rotating external magnet, and further comprising means, coupled to said upper end wall, for vertically adjusting said beam during rotation.

11. A sampling device as in claim 10 wherein said adjusting means comprises a sleeve mounted adjustably in height in said projection of said end wall, said agitator being mounted rotatably in said sleeve.

12. A sampling device as in claim 11 wherein said adjusting means further comprises:
   a tubular hollow attachment, disposed on an outside surface of said upper end wall proximate said projection, having internal threads, and having a vertical guide slot therein;
   an adjusting pin, adjustably disposed in said attachment, having threads engaging those of said attachment, and having a lower end with an annular groove therein extending into said sleeve,
      said sleeve having a threaded opening disposed in horizontal alignment with said annular groove; and
   a threaded bolt, screwed through said threaded opening in said sleeve, protruding into said vertical guide slot, and having an inner end extending into said annular groove.

13. A sampling device as in claim 1 wherein said bottom of said container comprises a plate disposed between said bottom of said container and said filter membrane, supporting said filter membrane, having a plurality of radial channels disposed on a bottom thereof, and having a plurality of holes disposed therethrough opening into said channels.

14. A sampling device as in claim 13 wherein an upper surface of said plate includes a downwardly inclined border, and further comprising a sealing ring disposed above and in contact with said border.

15. A sampling device as in claim 1 wherein said rotatable agitator comprises a horizontally disposed beam having a cross section tapered downwardly, and a lower end with a flow break-away edge.

16. A sampling device as in claim 1 wherein said second outlet is disposed at a highest point on an inside surface of said upper end wall, and wherein said upper end wall includes a projection disposed centrally therein and protruding into an inside of said container.

17. A sampling device as in claim 1 wherein said rotatable agitator comprises a horizontally disposed beam, and a magnet disposed in said beam so that said agitator is drivable by a rotating external magnet, and further comprising means, coupled to said upper end wall, for vertically adjusting said beam during rotation.

18. A sampling device as in claim 17 wherein said adjusting means comprises a sleeve mounted adjustably in height in said projection of said end wall, said agitator being mounted rotatably in said sleeve.

19. A sampling device as in claim 18 wherein said adjusting means further comprises:
   a tubular hollow attachment, disposed on an outside surface of said upper end wall proximate said projection, having internal threads, and having a vertical guide slot therein;
   an adjusting pin, adjustably disposed in said attachment, having theads engaging those of said attachment, and having a lower end with an annular groove therein extending into said sleeve,
      said sleeve having a threaded opening disposed in horizontal alignment with said annular groove; and,
   a threaded bolt, screwed through said threaded opening in said sleeve, protruding into said vertical guide slot, and having an inner end extending into said annular groove.

* * * * *

UNITED STATES PATENT AND TRADEMARK OFFICE
CERTIFICATE OF CORRECTION

PATENT NO. : 4,699,013

DATED : October 13, 1987

INVENTOR(S) : Karl-Heinz Kroner

It is certified that error appears in the above-identified patent and that said Letters Patent is hereby corrected as shown below:

On The Title Page:

Change the names and addresses of the Assignees from:
"Gessellshaft fur Bio technolgische
Forshung mbH, Braunschroeig, Fed.
Rep. of Germany; Intermedicat,
(GmbH), Emmenbrucke,
Switzerland"

to

--Gessellshaft fur Biotechnologische
Forschung mbH (GBF), Braunschweig
Fed. Rep. of Germany; and
Intermedicat GmbH,
Emmenbrucke, Switzerland.--

Signed and Sealed this

Fifth Day of July, 1988

*Attest:*

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO. : 4,699,013
DATED : October 13, 1987
INVENTOR(S) : Karl-Heinz Kroner

It is certified that error appears in the above-identified patent and that said Letters Patent is hereby corrected as shown below:

Title page:

Change the names and addresses of the Assignee from:

"Gessellshaft fur Biotechnologische
Forschung mbH (GBH), Braunschweig
Fed. Rep. of Germany; and
Intermedicat GmbH,
Emmenbrucke, Switzerland."

to

--Gesellschaft fur Biotechnologische
Forschung mbH (GBF), Braunschweig
Fed. Rep. of Germany; and
Intermedicat GmbH,
Emmenbrucke, Switzerland.--

This certificate supersedes certificate of correction issued July 5, 1988.

Signed and Sealed this

Tenth Day of January, 1989

*Attest:*

DONALD J. QUIGG

*Attesting Officer*     *Commissioner of Patents and Trademarks*